US00PP13147P2

(12) United States Plant Patent
Utecht

(10) Patent No.: US PP13,147 P2
(45) Date of Patent: Oct. 29, 2002

(54) GERANIUM PLANT NAMED 'FISBLIFIRE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,182

(22) Filed: Nov. 21, 2001

(65) Prior Publication Data

US 2002/0100102 P1 Jul. 25, 2002

(51) Int. Cl.[7] ..... A01H 5/00

(52) U.S. Cl. ..... Plt./332

(58) Field of Search ..... Plt./332

*Primary Examiner*—Kent L. Bell
(74) *Attorney, Agent, or Firm*—Foley & Lardner

(57) ABSTRACT

A new and distinct cultivar of geranium plant named 'Fisblifire', as described and illustrated, and particularly characterized by the combined features of brilliant red, single-type flowers, floriferous with large umbels, vigorous growth, well-branched plant habit and early flowering response.

1 Drawing Sheet

BOTANICAL CLASSIFICATION

*Pelargonium peltatum.*

VARIETY DENOMINATION

'Fisblifire'.

BACKGROUND OF THE INVENTION

The present invention comprises a new and distinct cultivar of geranium, botanically known as *Pelargonium peltatum*, and hereinafter referred to by the cultivar name 'Fisblifire'.

'Fisblifire' is a product of a planned breeding program which had the objective of creating new ivy geranium cultivars with single-type flowers, relatively vigorous, but well-branched growth habit, and various flower colors.

'Fisblifire' originated from a hybridization made by the inventor Angelika Utecht in a controlled breeding program in Galdar, Gran Canaria, Spain, in 1996. The female parent is an unpatented hybrid seedling, no. K95-823-9, having orange-red, single-type flowers, zoned foliage, and moderately vigorous growth.

The male parent of 'Fisblifire' was the unpatented hybrid seedling no. I95-305-1, which was derived from self-pollinating the unpatented variety 'Denise Huber'. 'Denise Huber' is characterized by red, semi-double flowers, medium-green foliage with strong zonation, and vigorous growth, but not very well branched growth habit. The seedling thereof had orange-red, semi-double flowers and more compact plant habit.

'Fisblifire' was selected as one flowering plant within the progeny of the stated cross by Angelika Utecht in 1997, in a controlled environment in Galdar, Gran Canaria, Spain. The first act of asexual reproduction of 'Fisblifire' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisblifire' are firmly fixed and are retained through successive generations of asexual reproduction. The new cultivar reproduces true to type.

'Fisblifire' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisblifire' in combination distinguish this geranium as a new and distinct cultivar:

1. Brilliant red, single-type flowers;
2. Large and floriferous inflorescences,
3. Medium-green foliage with distinct zonation;
4. Fairly vigorous growth, long-trailing, but well-branched plant habit; and
5. Early spring flowering response.

Of the many commercial cultivars known to the present inventor, the most similar in comparison to 'Fisblifire' is the patented variety 'Fizzard' (U.S. Plant Pat. No. 10,992). In comparison to 'Fizzard', 'Fisblifire' has an almost similar flower color with a trace of an orange-red hue, differently shaped leaves, and wider and somewhat stronger zonation on its leaves. The plant habit of 'Fisbilfire' is almost as long trailing, but internodes are shorter, and it has a higher number of branches (by about 25%) resulting in a more bushy and uniform, less open, plant habit. Spring flowering response of 'Fisblifire' is early, but not as early as the extremely early spring flowering response of 'Fizzard'.

BRIEF DESCRIPTION OF THE DRAWINGS

The accompanying photographic drawing shows typical flower and foliage characteristics of 'Fisblifire' with colors being as true as possible with an illustration of this type. The drawing shows a branch end with leaves, buds and inflorescences.

DETAILED BOTANICAL DESCRIPTION

In the following description color references are made to The Royal Horticultural Society Colour Chart (R.H.S.). The color values were determined indoors from plants developed in a green-house in May 2001, in Hillscheid, Germany. The measurements were taken in Langley, British Columbia, Canada (unless stated otherwise), in early Jul. 18, 2001, weeks after planting of rooted cuttings. The plants were grown in 8 inch containers and had not been pinched.

Inflorescence:
- *Type.*—Umbel.
- *Shape.*—Roughly semi-spherical.
- *Average diameter.*—121 mm.
- *Average depth.*—65 mm.
- *Peduncle length.*—189 mm.
- *Peduncle color.*—Light green, RHS 143 C, outdoors a slight tinge of brown may occur (RHS 179 B).
- *Pedicel length.*—27 mm with spur.
- *Pedicel color.*—Green, RHS 143 B, infused with brown, RHS 179 A.
- *Number of flowers per umbel.*—About 12–14 .

Corolla:
- *Average diameter.*—50 mm.
- *Form.*—Single.
- *Shape.*—Round outline, with the upper petals about the same size as the lower petals, petals not overlapping.
- *Number of petals.*—5.
- *Number of petaloids.*—None.
- *Shape of petals.*—Obovate, base acute, upper end is truncate or rounded, margin is entire.
- *Size of petals.*—Upper petals are 29–30 mm long, 17–18 mm wide; lower petals are 26–27 mm long, 18–19 mm wide.
- *Color (general tonality from a distance of three meters).*—Brilliant red.
- *Color of upper petals.*—Main part RHS 44 A to 45 B, bluish overtone near base RHS 74 C.
- *Markings of upper petals.*—Two dark purple veins, RHS 187 B.
- *Color of lower petals.*—Between RHS 44 A and RHS 45 B.
- *Markings of lower petals.*—None.
- *Color of lower surface of petals.*—Between RHS 46 C to 44 B.
- *Color of sepals.*—Outer surface light green, RHS 144 A; inner surface light green, RHS 144 B.
- *Number of sepals.*—5.
- *Shape of sepals.*—Linear to lanceolate, acute tip, truncate base, surface with moderate pubescence, margin entire.
- *Size of sepals.*—12–14 mm long, 4 mm wide for the largest upper sepal, 2–3 mm in width for the other sepals.

Bud (just before petals unfold):
- *Shape.*—Narrow elliptical to somewhat asymmetrical.
- *Color of sepals.*—Light green, RHS 143 C (Both surfaces).
- *Color of petals.*—Red RHS 45 B (Both surfaces).
- *Length.*—16–17 mm.
- *Width.*—6–7 mm.

Reproductive organs:
- *Androecium.*—7 fertile anthers, plenty of pollen production, yellow-orange, RHS 26 A, lower side of anthers blackish, RHS 187 A, filaments white, RHS 155 D, to light-pink, RHS 52 D.
- *Gynoecium.*—One pistil, whitish style, RHS 155 D to 65 D, stigma 5–6-lobed stigma, dark-red, RHS 53 A.

Fertility/seed set: Moderate seed set, mainly in late summer to fall; seed: oblong, 4–5 mm long, brown, RHS 177 B.

Fruit: Oblong, about 6 mm wide, rostrum (beak) 38–42 mm long.

Spring flowering response period: In Hillscheid, Germany, in 2000 plants had on average 0.9 flowers open 12 weeks after planting of rooted cuttings (early for pinched plants).

Outdoor flower production: Continuous and rich flowering, the flower count in 2000 in Hillscheid, Germany, indicated about 6–7 inflorescence per plant in mid May.

Durability: Good stability of flower color, good rain resistance.

Lastingness of the individual flower: About 7–8 days at 18° C., about 15 days for the umbel.

Fragrance: None.

PLANT

Foliage:
- *Shape.*—Ivy-shaped, with cordate base, with the gap between the lowest lobes mostly closed, apex rounded with moderate lobes, margin mostly entire, occasionally single, weak notches near the tips of lobes.
- *Texture.*—Upper surface smooth, glossy.
- *Size of leaf.*—83 mm wide, 51 mm long.
- *Color.*—Upper surface: Medium green, approximately RHS 137 C. Zonation: Brown, about RHS 166 A. Lower surface: Green, RHS 137 D.
- *Petioles.*—35–45 mm long, 3–3.5 mm diameter, light green in color, approximately RHS 143 C.

General appearance and form:
- *Stem color.*—Green, RHS 143 A to 143 B.
- *Internode length.*—30–50 mm.
- *Branching pattern.*—10.2 branches.
- *Length of plants.*—51.4 cm (18-week-old plants, as described) 85–90 cm (about 35-week-old plants) measured from the top of the soil (base of the main stem) to the tips of the branches (measured without inflorescence).

Pest/disease resistance/susceptibility: No observations to date.

I claim:

1. A new and distinct cultivar of geranium plant named 'Fisblifire', as described and illustrated herein.

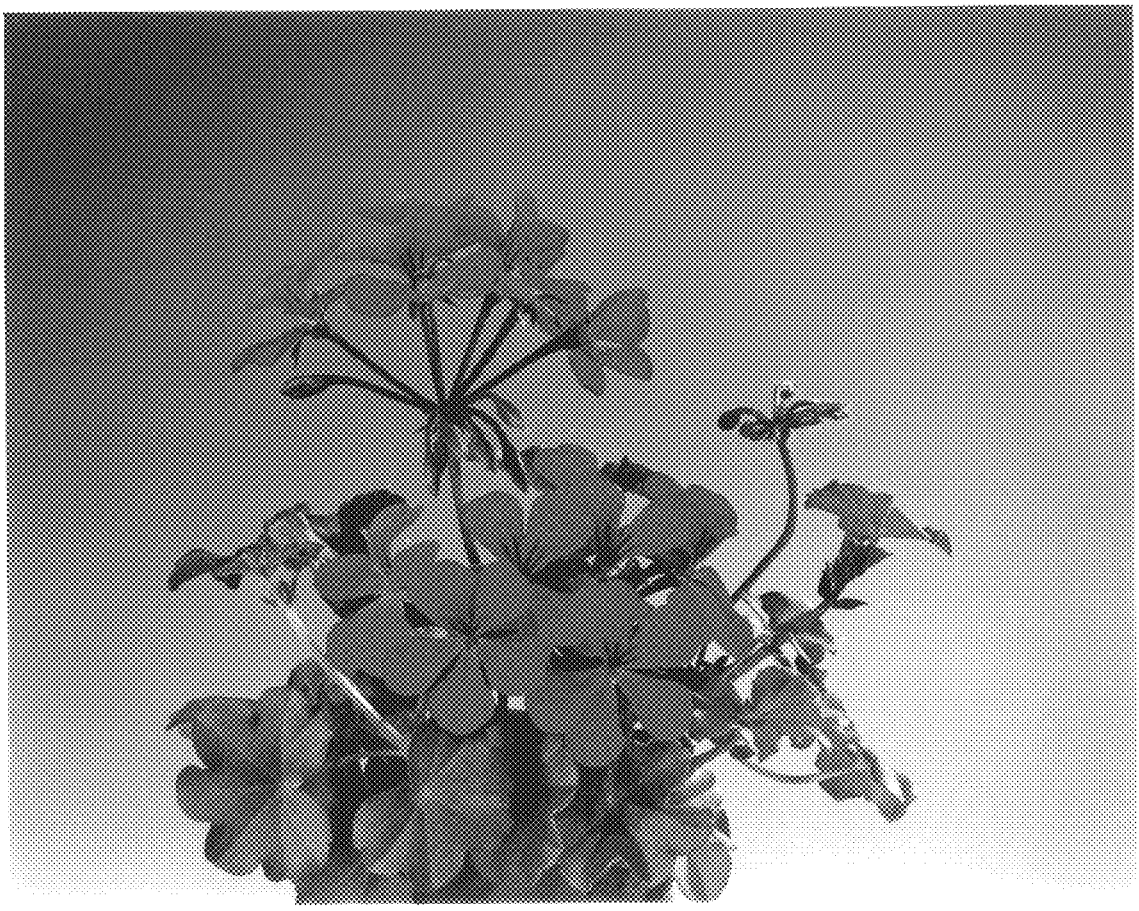

* * * * *